(12) United States Patent
Lopez et al.

(10) Patent No.: US 8,152,790 B2
(45) Date of Patent: Apr. 10, 2012

(54) CONNECTOR FOR MEDICAL USE

(75) Inventors: Georges-Antoine Lopez, Craponne (FR); Patrick Delorme, Chaponost (FR); Ludovic Allard, Millery (FR)

(73) Assignee: Cair LGL, Civrieuz d'Azergues (FR)

( * ) Notice: Subject to any disclaimer, the term of this patent is extended or adjusted under 35 U.S.C. 154(b) by 218 days.

(21) Appl. No.: 12/065,400

(22) PCT Filed: Dec. 4, 2006

(86) PCT No.: PCT/FR2006/051274
§ 371 (c)(1), (2), (4) Date: Feb. 29, 2008

(87) PCT Pub. No.: WO2007/066034
PCT Pub. Date: Jun. 14, 2007

(65) Prior Publication Data
US 2008/0249508 A1    Oct. 9, 2008

(30) Foreign Application Priority Data
Dec. 5, 2005 (FR) ..................................... 05 53720

(51) Int. Cl.
*A61M 25/16* (2006.01)
(52) U.S. Cl. ....................................................... 604/533
(58) Field of Classification Search .......... 604/533–537, 604/284, 249; 285/390
See application file for complete search history.

(56) References Cited

U.S. PATENT DOCUMENTS 6,325,782 B1 * 12/2001 Lopez ........................... 604/249
6,669,673 B2    12/2003 Lopez
2002/0032433 A1  3/2002 Lopez
(Continued)

FOREIGN PATENT DOCUMENTS
EP    0390771 A1    4/1989
(Continued)

OTHER PUBLICATIONS

International Search Report (PCT/ISA/210) for corresponding International Application No. PCT/FR2006/051274 dated Apr. 3, 2007.
(Continued)

*Primary Examiner* — Jackie Ho
*Assistant Examiner* — Imani Hayman
(74) *Attorney, Agent, or Firm* — Heslin Rothenberg Farley & Mesiti P.C.; Victor A. Cardona

(57) ABSTRACT

A connector for medical use includes an adapter equipped at its center with a needle extending into a chamber and optionally terminating in a part of a terminal end of the chamber. The terminal end has a cross section suitable for receiving, by friction, a luer type male connector. The needle a terminal part including an orifice or orifices, which is encased in a cavity of an elastic seal having, in the thickness of its free end, a slit or equivalent. The elastic seal has a free end at a tangent to that of the chamber and is provided with a ring encircling its terminal part at least as far as the zone opposite the orifice or orifices of the needle. Along part of the length of the terminal end of the chamber, the outer surface of the elastic seal and/or the inner surface or thickness of the ring has at least one recess for promoting the expulsion of the material constituting the seal, at the time of passage of the needle.

20 Claims, 7 Drawing Sheets

U.S. PATENT DOCUMENTS

| | | |
|---|---|---|
| 2002/0138047 A1 | 9/2002 | Lopez |
| 2004/0217315 A1 | 11/2004 | Doyle |
| 2005/0151105 A1 | 7/2005 | Ryan et al. |
| 2007/0088325 A1* | 4/2007 | Fangrow .................. 604/533 |

FOREIGN PATENT DOCUMENTS

| | | | |
|---|---|---|---|
| EP | 0544581 | A1 | 6/1993 |
| EP | 0748635 | A2 | 12/1996 |
| EP | 0681493 | B1 | 6/2000 |
| EP | 0781151 | B1 | 6/2003 |

OTHER PUBLICATIONS

Written Opinion (PCT/ISA/237) for corresponding International Application No. PCT/FR2006/051274 dated Apr. 3, 2007.

* cited by examiner

CONNECTOR FOR MEDICAL USE

CROSS REFERENCE TO RELATED APPLICATIONS

This application is a national stage of PCT International Application No. PCT/FR2006/051274, filed on Dec. 4, 2006, and published in French on Jun. 14, 2007, as WO 2007/066034 A1, which claims priority from French patent application No. FR 0553720, filed on Dec. 5, 2005, the entire disclosures of which are incorporated herein by reference.

The invention relates to a connector for medical use. The connector concerned is of the type having a first end also called "upstream end" for connection to a nozzle in which a fluid flows; and a second end, also called "downstream end" for cooperating with a device for withdrawing or injecting the said fluid via a connector of the luer male type. In the rest of the description, reference is made to the expressions "upstream end" and "downstream end" regardless of the fluid flow direction.

In practice, in a manner known per se, the device has a chamber joined at one of its ends with an adapter constituting the upstream end of the actual connector, the other end of the chamber being conformed for receiving, by friction, the tip of the luer type male connector. The passage of the liquid between the nozzle connected to the upstream end of the connector and the end of the luer male connector is provided via a needle joined to the adapter and terminating in the chamber.

Connectors of this type have been widely described, one of the essential difficulties being to ensure a satisfactory seal of the connection with the tip of the syringe.

The devices presumed to meet this requirement are, for example, those described in document EP-A-148 635. This document in fact describes a flap connector equipped with an elastically deformable piston head maintained in a position directly adjacent to the downstream junction adapter, the piston itself delimiting a chamber inside which the needle is placed. In the inactive position of the connector, the piston head is in its deformed state, thereby causing the blocking of the orifice and hence the closure of the chamber. On the contrary, in the active position, the piston head is in its undeformed state, the outlet orifice of the piston head then remaining open so that the needle can pass through it. In other words, a quantity of liquid corresponding substantially to the volume of the chamber remains permanently in the said chamber, the risk being that part thereof may flow via the orifice under the action of the pressure.

Document EP-A-681 493 describes a medical valve equipped with an elastic seal, here also adjacent to the wall of the free end of the connector and suitable for being compressed under the action of the thrust exerted by the fluid injection or withdrawal device.

In a particular embodiment and unlike the preceding document, the seal covering the needle is in contact therewith along its whole height serving to prevent the formation of a residual volume in the inactive position. The compression of the elastic seal accordingly serves to uncover the end of the needle and thereby to free its orifices to enable the transfer of the fluid into the syringe.

Document EP-A-544 581 describes a connector comprising a spring equipped at its centre with a needle surmounted by an elastomer plug, the said plug being capable of sliding in the connector body between a rest position and an active position. In practice, the plug is traversed by the said needle in the active position of the system, while it is blocked in the rest position, the spring constituting the elastic means causing the movement of the plug.

The main drawback of these various devices, whereof the common principle is to arrange an elastic spring directly in contact with the chamber walls, is the failure to guarantee an optimal seal, due in particular to the too limited radial tightness associated with the very nature of the elastic material.

Document EP-A-309 771 describes a connector equipped not with a needle but with a hollow needle having a flat end, encased in an elastic seal, the seal being surmounted at its downstream end, by a plastic clamping bush. It appears from the figures that part of the elastic seal remains in contact with the chamber walls, thereby preventing, owing to the high friction force, a uniform and regular guiding of the said elastic seal and hence a constant fluid transfer. Furthermore and above all, with regard to the radial clamping force applied to the end of the elastic seal, in view of the arrangement of the bush, the seal, and the hollow needle, a high resistance of the seal can be expected at the time of introduction of the end of the syringe and hence a difficult passage of the hollow needle through the terminal slit.

The Applicant has sought to improve the systems described in these documents, with the main objective of ensuring an optimal seal of the connector and a constant fluid transfer in the active position.

For this purpose, the Applicant has improved the ring connector as previously described, by providing, in the zone between the end of the needle and the end of the elastic seal, a recess of the seal and/or of the ring, thereby serving to expel the material at the time of passage of the needle, without necessarily jeopardizing the tightness of the system.

In other words, the subject of the invention is a connector for medical use comprising an adapter equipped at its centre with a needle extending into a chamber and optionally terminating in part of the terminal end of the said chamber, the said terminal end having a cross section suitable for receiving, by friction, a luer type male connector, the needle being encased and maintained at least in its terminal part including the orifice in the cavity of an elastic seal having, in the thickness of its free end, a slit or equivalent, the elastic seal having a free end at a tangent to that of the chamber and being provided with a ring encircling its terminal part at least as far as the zone opposite the orifice or orifices of the needle.

This connector is characterized in that along part of the length of the terminal end of the chamber, the outer surface of the elastic seal and/or the inner surface or thickness of the ring has at least one recess for promoting the expulsion of the material constituting the seal, at the time of passage of the needle.

In practice, the ring extends, upstream of the orifice or orifices of the needle, along a length shorter than 3 mm, in practice, about 2 mm.

According to the invention, the recess may thus be formed on two distinct parts. Thus, the recess may be formed exclusively on the outer surface of the elastic seal. It may also be formed exclusively on the inner surface of the ring or in the thickness of the ring. In the latter case, it constitutes an open recess. It may also be formed in the two elements. In this case, the recess provided in the elastic seal is advantageously opposite the recess provided in the ring, in order to optimize the material expulsion process.

The number of recesses is not limited.

In a preferred embodiment, the outer surface of the elastic seal has an annular recess while the ring, in its thickness, has two symmetrically distributed recesses.

The orifice or orifices of the needle may be provided at a plurality of locations.

In a first embodiment, the needle has a conical, plane or rounded end and is provided with a terminal orifice.

To ensure the smooth passage of the needle in the slit, the recess or recesses are formed in a zone downstream of the end of the needle.

To ensure the tightness of the system, that is, the clamping of the elastic seal causing the closure of the slit, the outer cross section of the seal in contact with the ring downstream of the recess, is larger than the corresponding inner cross section of the ring. On the other hand, upstream of the recess or recesses, the outer cross section of the seal is substantially equal to the inner cross section of the ring.

Furthermore, to ensure the tightness between the needle and the elastic seal in the unconnected position of the connector, the needle has a cross section larger than the corresponding inner cross section of the seal, that is, the cross section of the cavity, along the whole part of the seal encircled by the ring. Upstream of this zone, the needle has a cross section substantially equal to or lower than the corresponding inner cross section of the seal.

Similarly, to promote the penetration of the slit by the needle, the cavity of the elastic seal in which the needle is maintained may be longer than the needle, in practice, a few millimeters (maximum 2 mm).

In another embodiment, the needle has a conical, plane or rounded end and is provided with at least one, advantageously two side orifices opposite one another.

To ensure the smooth passage of the needle in the slit, the recess or recesses are formed in a zone downstream of the end of the needle.

In this embodiment, the tightness is not provided at the slit but at the side orifices.

In this case, the outer cross section of the seal, to the exclusion of the recess, is substantially equal to the inner cross section of the ring, along the whole length of the ring.

On the other hand, and similarly to above, the needle has a cross section larger than the corresponding inner cross section of the seal, along the whole part of the elastic seal encircled by the ring. Upstream of this zone, the needle has a cross section substantially equal to or lower than the corresponding inner cross section of the seal.

Insofar as the orifices are perpendicular to the fluid flow, and the needle is subject in this zone to the stress of the elastic seal, there is no possibility of liquid reflux. The tightness is therefore optimal.

The body of the needle may have various forms, such as for example, a tubular form, a conical form with or without a stepped shoulder, the end optionally being plane, pointed (conical) or rounded.

According to the invention, the seal may cover all or part of the needle. In an advantageous embodiment, it covers the whole length of the needle.

When the seal does not cover the whole needle, the said seal is joined by any elastic means and particularly a spring, which bears on the base of the adapter.

To improve its flexibility and thereby promote the release of the needle, the said elastic seal, in its mid-portion, has at least one, advantageously two side slits.

In another embodiment, the upstream end and the mid-portion of the seal have a generally conical shape, the wall of the seal in this zone being in the form of a succession of beads or ripples.

Similarly, to ensure the guidance of the seal in the chamber, the said elastic seal has no contact point with the side walls of the chamber. Accordingly, the guidance is provided by the ring alone, whereof all or part of the wall is in sliding contact with the corresponding wall of the chamber throughout the movement of the elastic seal, from its rest position to its compressed position. Due to the plastic nature of the materials used, only a minimum friction force exists between the chamber and the ring.

The elastic seal is in fact advantageously prepared from an elastomer, such as for example silicone or thermoplastic, and more generally from any material capable of imparting a sufficient elasticity to it to permit the release of the needle, while ensuring, in the rest position, the tight closure, depending on the embodiments, at the slit or at the side orifices.

In practice, the ring is fabricated from a rigid or semi-rigid material.

In a first embodiment, it is fabricated separately to then be combined with the elastic seal before installation in the connector.

In a second embodiment, the elastic seal-ring combination is a two-material combination, that is, fabricated in a single mould using two distinct materials.

In a preferred configuration, the chamber has at least two compartments with different cross sections, respectively a central compartment having a constant inner cross section, at least in the zone corresponding to the stroke of the ring, and a terminal compartment constituting the terminal end, having a lower and constant or variable inner cross section, the ring extending partly into the central compartment in the rest position of the connector.

In practice, the inner cross section of the terminal compartment may be cylindrical or of the luer female type, that is, having a 6% luer taper. To promote the guidance of the elastic seal, the part of the ring contained in the central compartment has a cylindrical shape. On the other hand, in the central compartment, the ring may have a distinct shape, which depends on the shape of the inner cross section of the said compartment.

The invention and its advantages will appear clearly from the exemplary embodiments below, in conjunction with the appended figures.

FIG. 1 shows a perspective view of the connector of the invention. The said connector consists of three distinct parts, respectively an adapter (1), a chamber (2) comprising a first compartment (2a), a central compartment (2b) and a terminal compartment (2c), and a ring-elastic seal combination (3) (see also FIG. 7).

Figure 1:
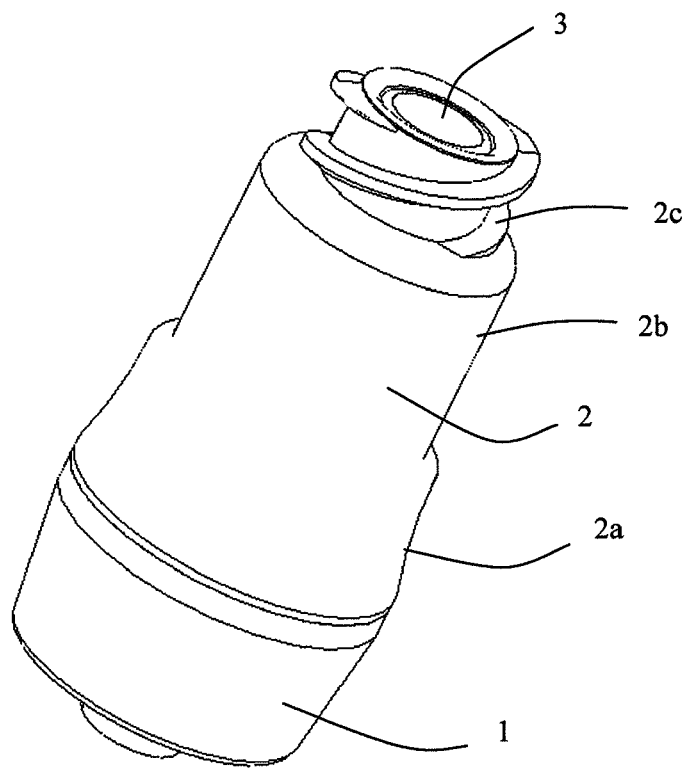
FIG. 1 shows a perspective view of the connector of the invention covering two possible embodiments according to the type of needle, that is, with a terminal orifice, or with side orifices.
Figure 2:
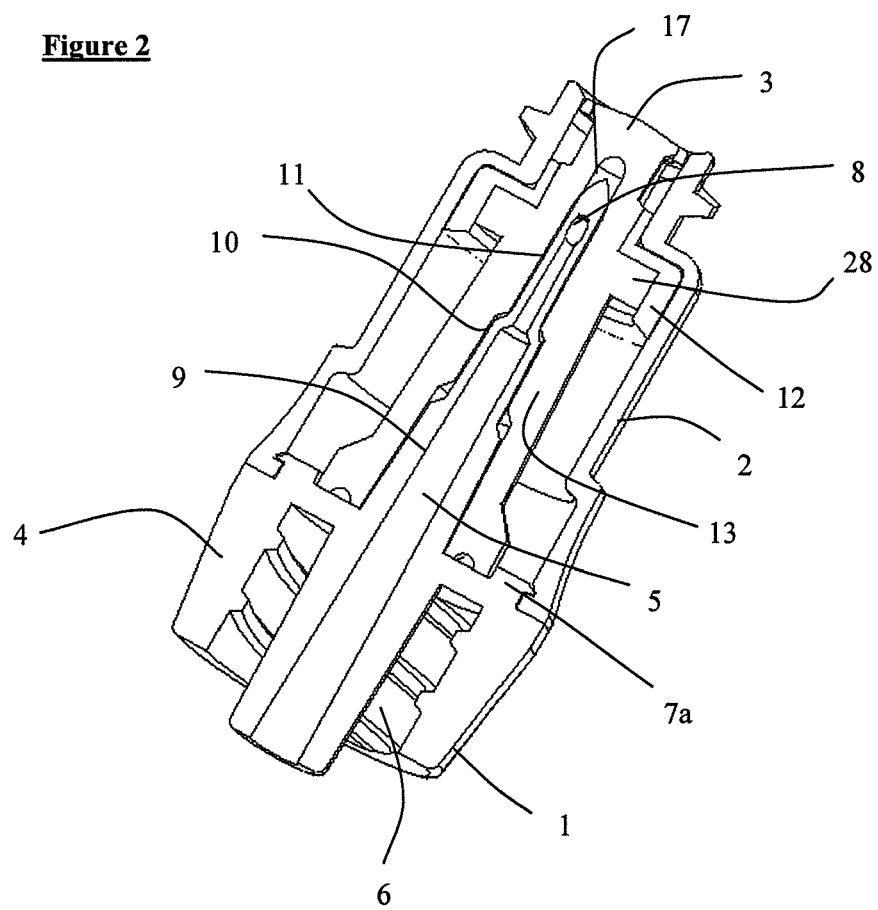
FIG. 2 shows a cross section of FIG. 1, when the needle has two side orifices and in which the elastic seal is in the pre-stressed position.
Figure 3:
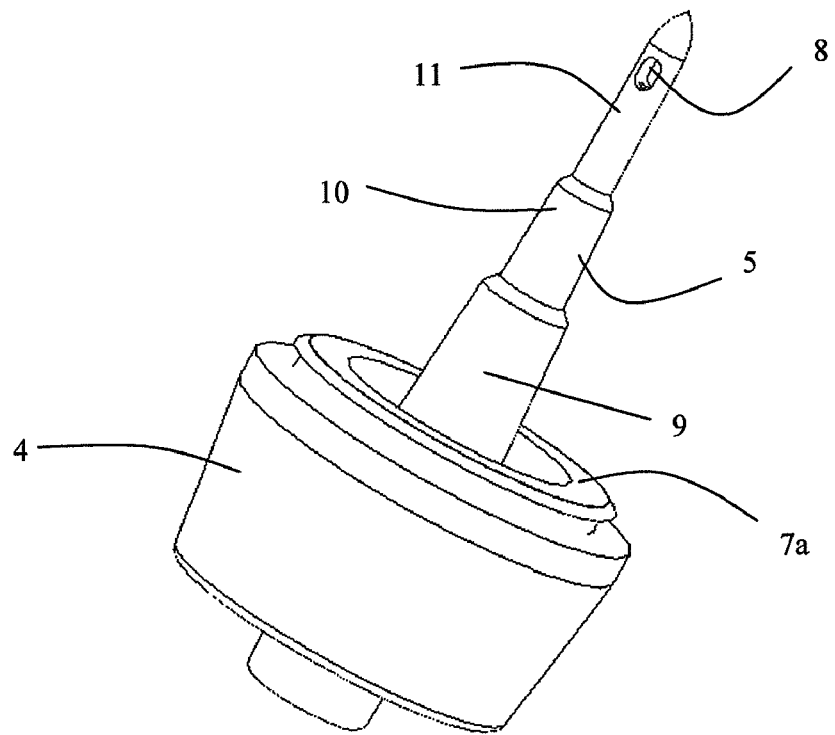
FIG. 3 shows a perspective view of the adapter-needle combination of FIG. 2.

These three associated elements are found, shown in FIG. 2, in a cross section, in the rest position of the elastic seal in the embodiment in which the needle has two side orifices.

More precisely, the adapter (1) is in the form of a composite part associating the actual adapter body (4) and the needle (5). The adapter body is further equipped with an internal screw thread (6) for cooperating with a corresponding screw thread of a luer female connector in which a fluid may flow. The said adapter is further equipped with a clip (7a) for cooperating with a corresponding shape (7b), arranged at the base of the first chamber (2a). The actual needle (5) is equipped, close to its free end, itself blocked, with two side orifices (8) through which the fluid flows. The said needle also has, from its base to its free end, three lengths (9, 10, 11) having a decreasing conical cross section separated by shoulders, for promoting its release under the action of the thrust exerted by the luer type male connector on the ring/elastic seal combination (3).

Figure 4:
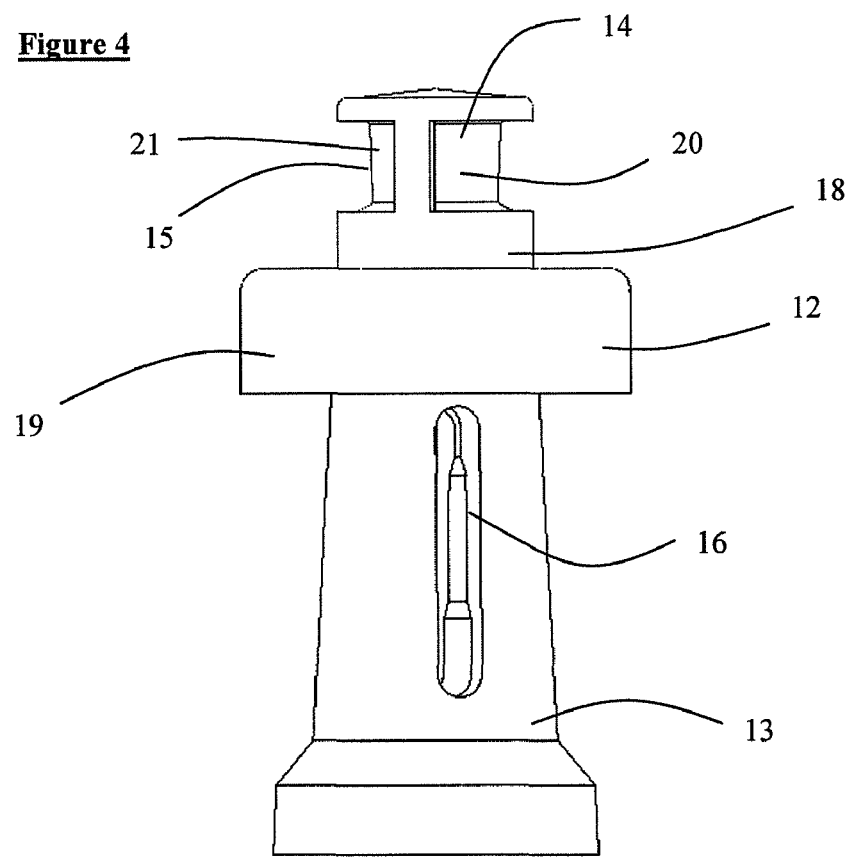
FIG. 4 shows a perspective view of the elastic seal-ring combination.
Figure 5:
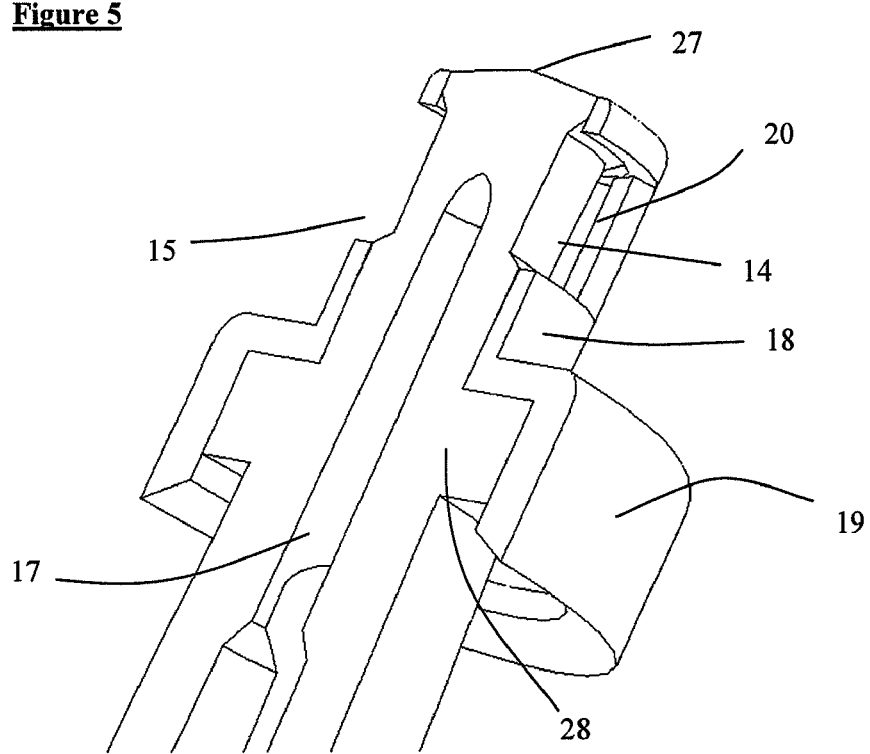
FIGS. 5 and 6 show cross sections of FIG. 4.
Figure 6:
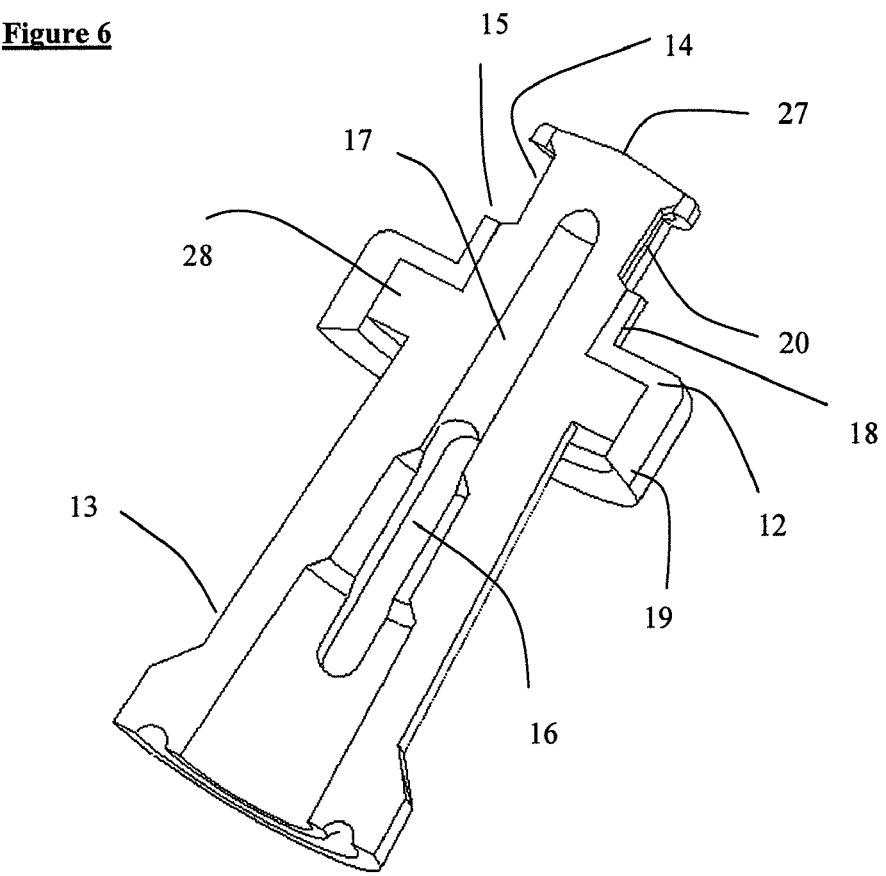

FIGS. 4, 5 and 6 show the body of the invention, that is, the ring (12)-elastic seal (13) combination. More precisely, the elastic seal is in the form of a tube having a conical outer cross section, for extending into the chamber (2a) from the base of the adapter (1) to the free end of the terminal chamber (2c). The elastic seal is not in contact at any point with the chamber (in the uncompressed position). To take account of the shape and dimensions of the central chamber in combination with the guiding function of the ring, the seal, close to the downstream end of the central chamber (2b), has a collar (28) encircled by the ring (12). The said elastic seal is made from silicone and, close to its free end, has a recess (14) and a slit (27). As it appears in FIG. 2, the recess is upstream of the end of the needle in the uncompressed position of the elastic seal. To improve its flexibility and promote its movement both under the action of the thrust exerted on the ring, and also at the time of its repositioning, the elastic seal is provided with two side slits (16), opposite one another, arranged on its mid-portion. Furthermore, as shown in FIGS. 5 and 6, the elastic seal, at its centre, has a cavity (17) having a shape corresponding to that of the needle, the cavity however being slightly longer than the needle.

In the embodiment shown in FIG. 2, the inner cross section of the elastic seal is larger than the cross section of the needle except in the terminal zone of the needle covered by the ring and including the side orifices, where the inner cross section of the elastic seal is lower than the cross section of the needle.

The ring (12) is shown in particular in FIGS. 4 and 5. It is positioned at the end of the elastic seal (13) and has two lengths of different cross sections, respectively a first cylindrical length (18) encircling the terminal part of the elastic seal along a length corresponding to the length of the terminal compartment and having a cross section substantially equal to the cross section of the said compartment, and a second cylindrical length (19) having a larger cross section substantially equal to the corresponding cross section of the central chamber (2b) and covering the collar (28) of the elastic seal. The ring (12) is made from a rigid or semi-rigid material, optionally of a bi-material with the elastic seal, or separately, the ring and seal being joined to one another in particular by adhesive or by simple application. In the embodiment in which the holes of the needle are provided laterally (FIG. 2), the outer cross section of the seal is substantially equal to the inner cross section of the ring along their overlapping zone.

As shown in FIGS. 4, 5 and 6, the terminal part (18) of the ring (12) has two open recesses (15, 20) for promoting the expulsion of the plastic at the time of passage of the needle under the action of the thrust created by the installation of the luer type male connector.

Figure 7:
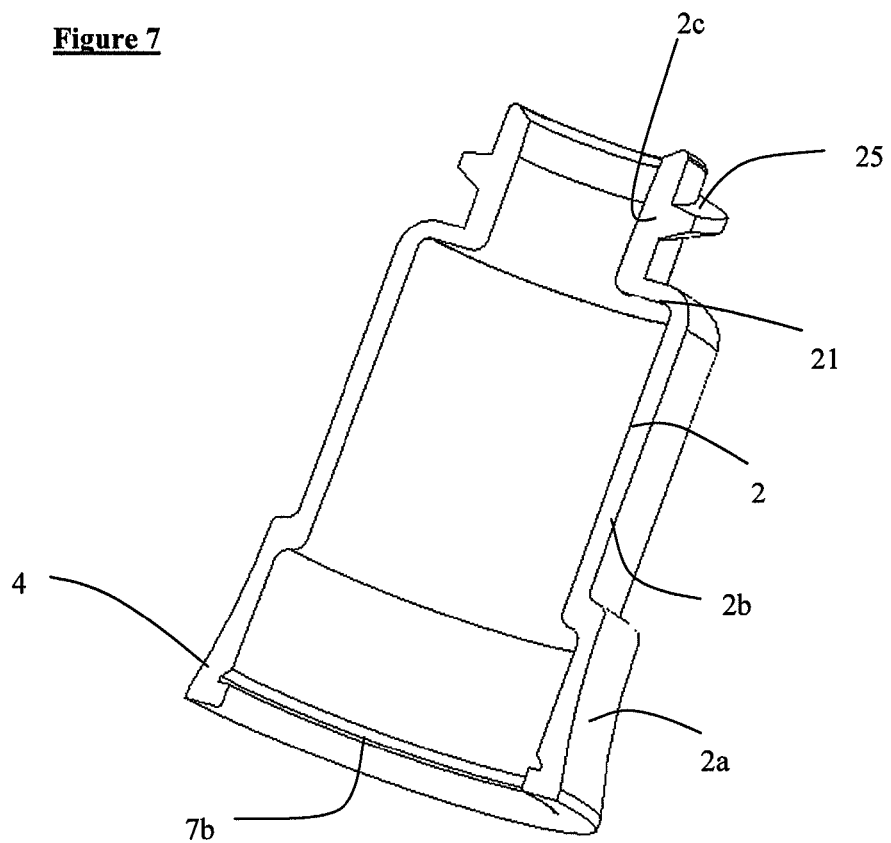
FIG. 7 shows a cross section of the chamber.

As shown in FIG. 7, the central compartment (2b) and the terminal compartment (2c) are connected by a shoulder (21) serving as a stop of the elastic seal in the rest position, thereby guaranteeing that the end of the elastic seal is at a tangent to the end of the terminal chamber (in the rest position).

FIG. 2 shows the arrangement of these various parts together, in the rest position of the elastic seal-ring combination. More precisely, in such a position, the entire outer surface of the ring is in sliding contact with the corresponding inner surface of the central and terminal chambers of the connector. In this configuration, the part (19) of the ring having a larger cross section is stopped, as already stated, against the corresponding shoulder (21) of the connector. In the same position, the elastic seal has no contact point with the sides of the chamber. Moreover, owing to the choice of the cross sections of the various elements, no radial force is exerted by the ring on the elastic seal (substantially equal cross sections), the closure of the orifices being provided by the radial force of the elastic seal exerted on the needle (seal cross section lower than needle cross section).

Figure 8:
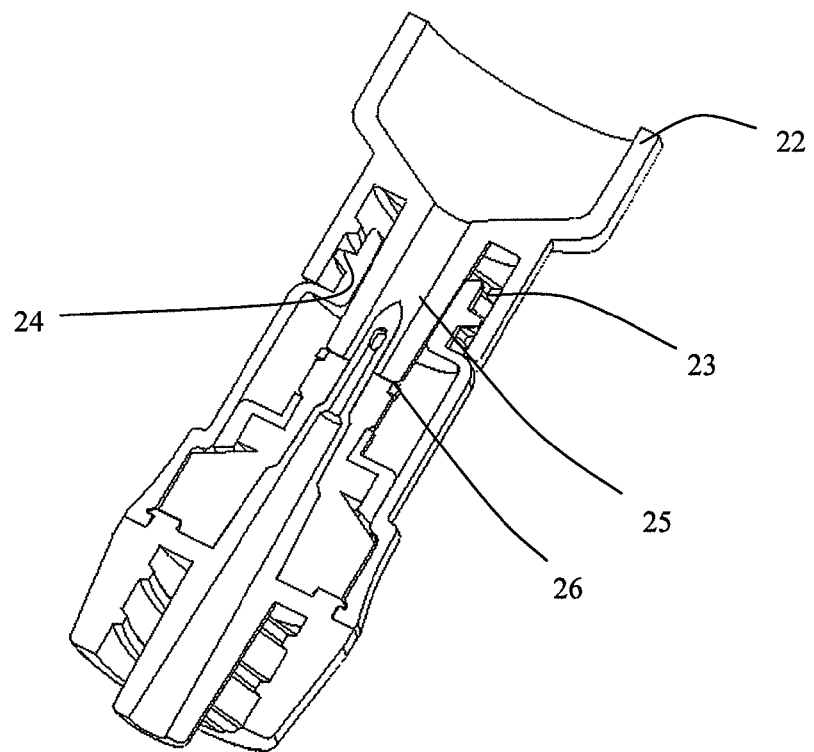
FIG. 8 shows a cross section of the connector in the compressed position of the elastic seal, that is, after connecting the luer type male connector. In this embodiment, the needle has side orifices.

The connected position is shown more precisely in FIG. 8 through the installation of a luer type male connector (22). The said connector has a screw thread (23) cooperating with the corresponding screw thread (24) of the terminal chamber (2c), thereby serving to ensure an effective fastening of the fluid injection or withdrawal device via the luer connector. The connector is further equipped with a luer cone (25) for insertion into the slot of the terminal chamber (2c). In practice, the cone (25) bears via its end (26) on the free end of the ring-elastic seal combination. The said bearing causes the movement of the elastic seal along the barrel of the needle in the direction of the adapter, followed by the passage of the tip of the needle through the slit (27) facilitated by the recesses, and finally, the liberation of the side orifices and hence the passage of the fluid.

In the connected position, the free part of the needle is therefore entirely contained in the inner channel of the cone (25), thereby permitting the fluid to flow from connector to connector. The movement of the ring during this operation is a homogeneous and uniform axial motion through the permanent contact of the walls of the cross section (19) of the ring with the central chamber (2b) throughout the movement, with a minimum of friction. As shown in FIG. 8, in the compressed position of the elastic seal, the small section part of the ring is neither in contact with the terminal chamber, nor with the central chamber. On the other hand, in this case, the elastic seal is in contact with the side walls of the chamber. In practice, the volume of the chamber is provided to be able to contain the volume of the seal in the compressed position.

Figure 9:
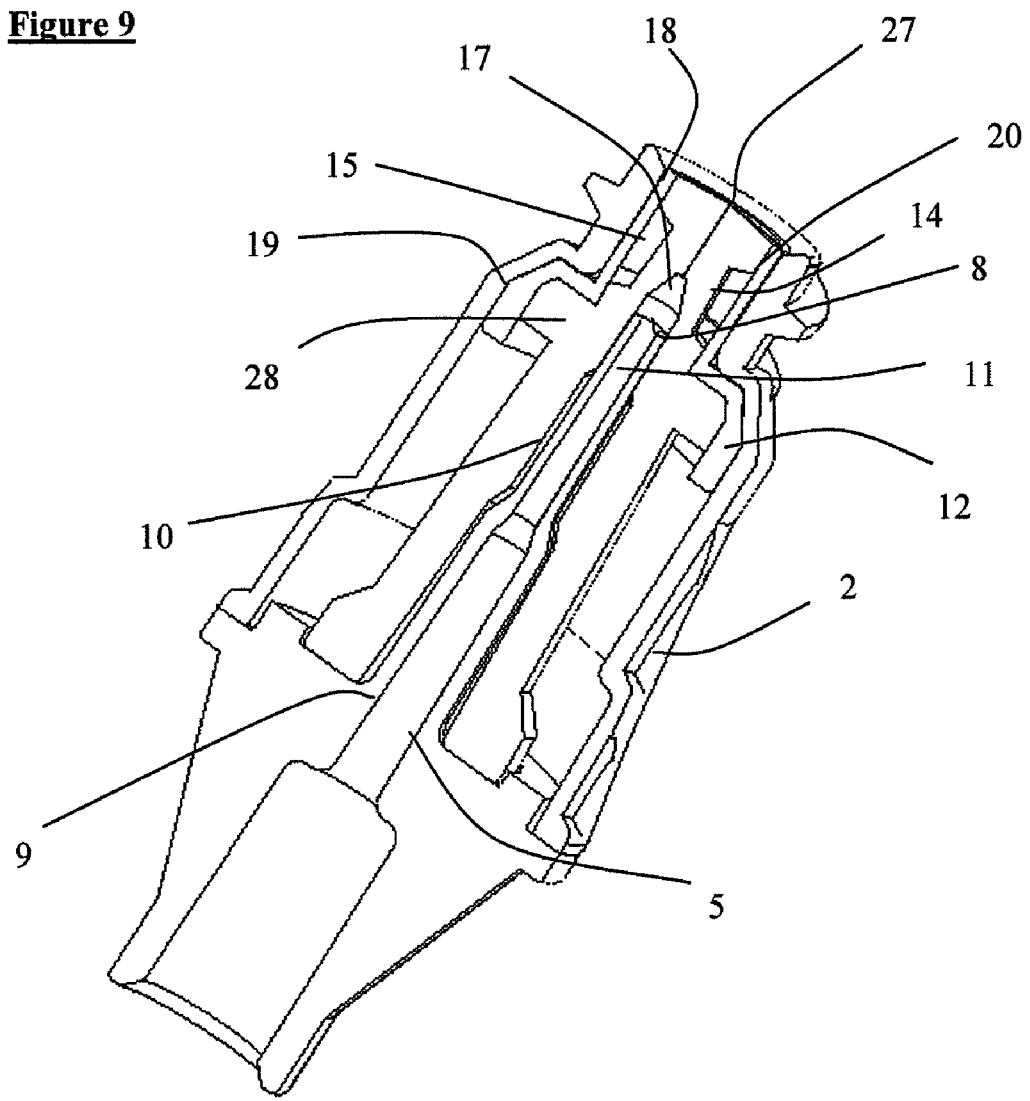
FIG. 9 shows a second embodiment in which the orifice of the needle is terminal.

FIG. 9 shows the embodiment in which the orifice of the needle is terminal. In this particular case, the free end of the needle is a plane end. To promote the insertion of the said needle into the slit, the cavity is slightly longer than the needle (2 mm more). Unlike the embodiment with two side orifices, the tightness is ensured not at the orifice of the needle, but at the slit. To obtain this tightness, a radial force is exerted by the ring (12) to the end of the elastic seal, the part (18) having an inner cross section lower than the outer cross section of the elastic seal. On the other hand, the outer cross section of the elastic seal at the collar (28) is substantially equal to the inner cross section of the part (19) of the ring, insofar as the tightness is not required at this level. At the same time, the inner cross section of the seal, along the length of the needle upstream of the ring, is larger than the cross section of the said needle. In the part opposite the ring, the inner cross section of the elastic seal is lower than the cross section of the needle.

Figure 10:
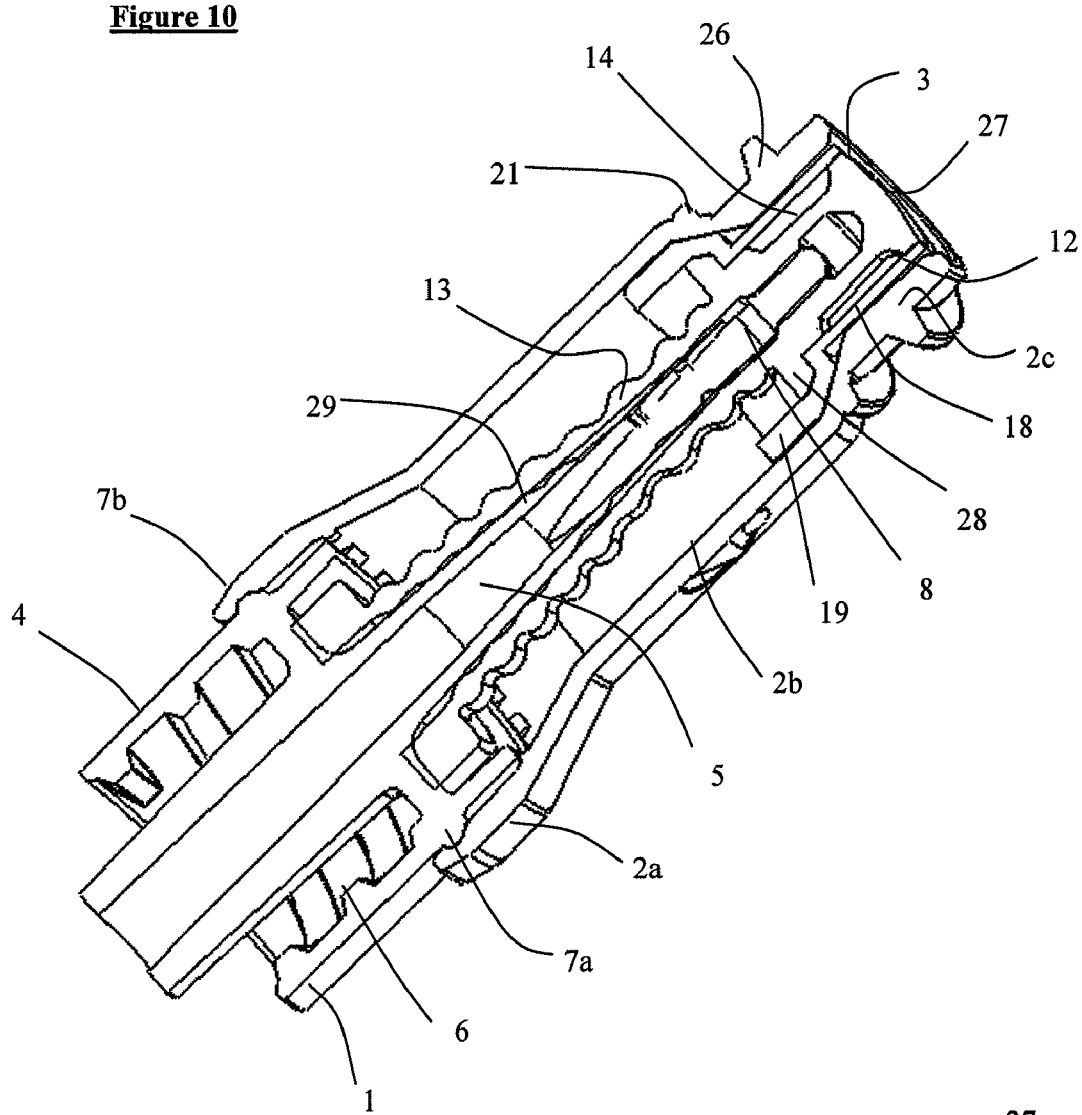
FIG. 10 shows a cross section of the connector of the invention, in which the elastic seal has a succession of ripples.
Figure 11:
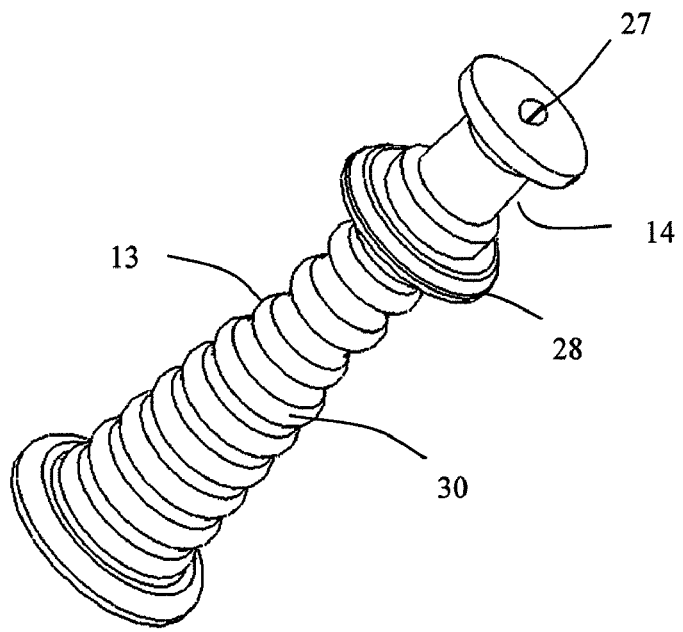
FIG. 11 shows a perspective view of the elastic seal of FIG. 10.
Figure 12:
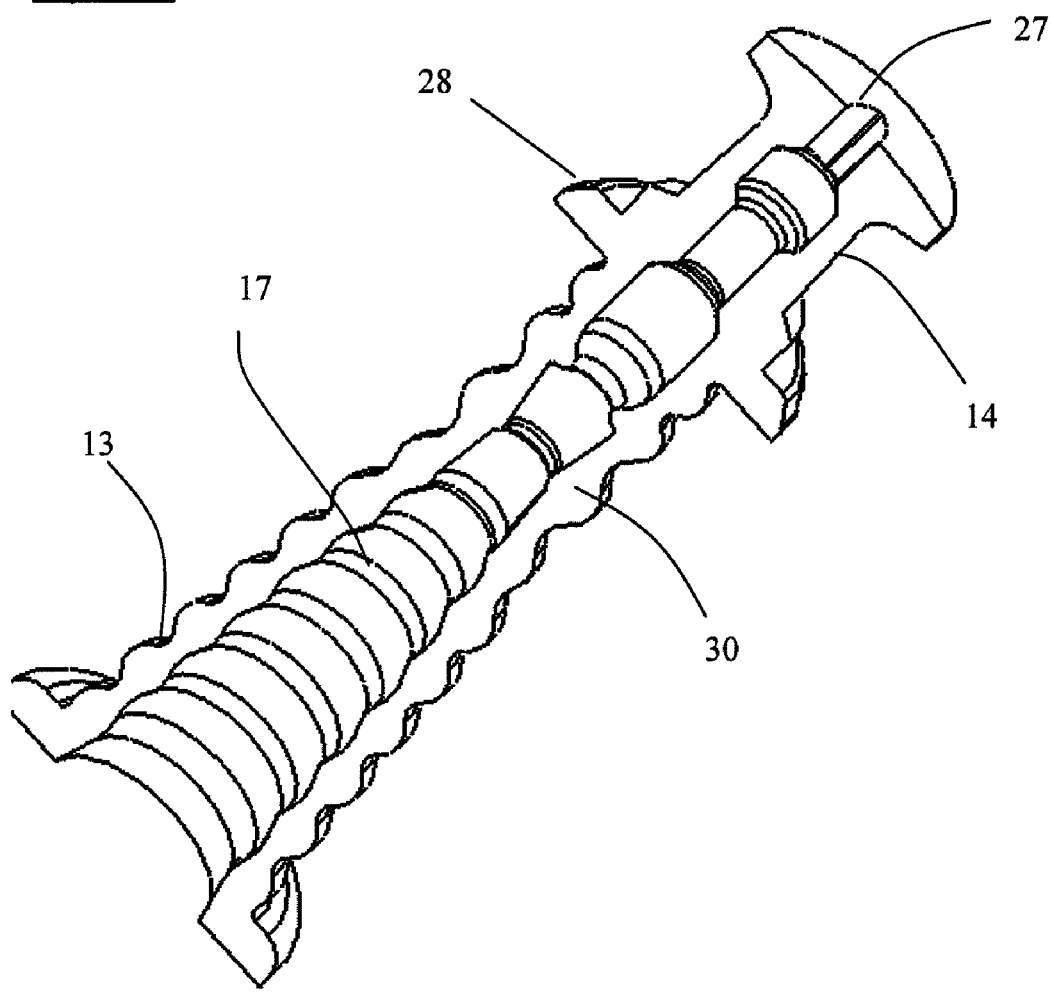
FIG. 12 shows a cross section of FIG. 11.

FIGS. 10 to 12 show another embodiment of the connector of the invention, which is distinguished from the preceding embodiment essentially in three points, respectively:

shape of the needle,
shape of the ring,
shape of the elastic seal.

First concerning the needle (5), it has a conical cross section (29) with a decreasing taper from the base of the connector to its free end. Unlike the preceding embodiment, there are no increments here, because the release of the needle, under the action of the thrust exerted by the luer type male connector, is facilitated by the actual shape of the elastic seal (see below).

Next concerning the ring (12), it still has two lengths having different cross sections, respectively:

a first cylindrical length (18) encircling the terminal part of the elastic seal along a length corresponding to the length of the terminal compartment and having a cross section substantially equal to the cross section of the said compartment, and a second cylindrical length (19) having a cross section substantially equal to the corresponding cross section of the central chamber (2b).

Unlike the preceding embodiment, the ring in its length (18), does not have an open recess, but on the contrary, has a continuous wall without any recess.

Finally concerning the elastic seal, in its terminal part, it has a shape identical to that described and shown in FIGS. 1 to 9, that is, in the direction of its terminal end, a collar (28), a recess (14) and a slit (27). On the other hand, the said elastic seal is distinguished from the one previously described in the shape of the mid-portion and the upstream end, that is, in the shape upstream of the collar (28). This in fact has a conical configuration, the seal wall being provided with successive ripples (30). This specific shape confers on the elastic seal an improved flexibility, promoting its movement both under the action of the thrust exerted by the ring, and also at the time of its repositioning.

The advantages of the invention clearly appear from the above description. Particularly noteworthy is the total tightness of the system obtained upstream of the terminal slit of the connector.

The invention claimed is:

1. A connector for medical use comprising:
   an adapter equipped at its centre with a needle extending from a first chamber into a second chamber and terminating in a terminal portion of said second chamber,
   said terminal portion having a cross section suitable for receiving, by friction, a luer type male connector at least in a terminal part of the needle including at least one orifice thereof being encased in a cavity of an elastic seal having, in the thickness of its free end, a slit or equivalent,
   the elastic seal having a free end at a tangent to a terminal end of the second chamber, said terminal end being at a longitudinal endpoint of said second chamber opposite said first chamber, relative to a longitudinal dimension of said second chamber;
   a ring encircling a terminal part of said seal at least as far as a zone opposite the at least one orifice of the needle, said ring extending from said terminal end of the second chamber to said first chamber and the ring located inside the second chamber; and
   wherein along a part of a length of the terminal portion of the chamber, at least one of the outer surface of the elastic seal and the inner surface or thickness of the ring has at least one recess for promoting the expulsion of a material portion of the seal into said recess, at a time of passage of the needle.

2. The connector according to claim 1, wherein the recess is formed on the outer surface of the elastic seal and in the thickness of the ring.

3. The connector according to claim 1, wherein the outer surface of the elastic seal has an annular recess and the ring, in its thickness, has two symmetrically distributed recesses.

4. The connector according to claim 1, wherein the recess is formed exclusively on the outer surface of the elastic seal.

5. The connector according to claim 1, wherein the needle has a conical, plane or rounded end and comprises a terminal orifice.

6. The connector according to claim 5, wherein an outer cross section of the seal in contact with the ring downstream of the recess is larger than a corresponding inner cross section of the ring.

7. The connector according to claim 5, wherein upstream of the at least one recess, the outer cross section of the seal is substantially equal to an inner cross section of the ring.

8. The connector according to claim 1, wherein the needle has a conical, plane or rounded end and comprises two side orifices facing one another.

9. The connector according to claim 8, wherein along the whole length of the ring, an outer cross section of the seal, to the exclusion of the recess, is substantially equal to an inner cross section of the ring.

10. The connector according to claim 5, wherein the at least one recess is formed in a zone downstream of an end of the needle.

11. The connector according to claim 5, wherein;
    the needle has a cross section larger than a corresponding inner cross section of the seal, along a whole part of the elastic seal encircled by the ring, and
    the needle has a cross section substantially equal to or lower than the corresponding inner cross section of the seal upstream of said part.

12. The connector according to claim 1, wherein the elastic seal covers an entire length of the needle and has two side slits formed in a mid-portion of said seal.

13. The connector according to claim 1, wherein the elastic seal covers an entire length of the needle and has a conical shape, and a wall of said seal, in a mid-portion of said seal and at an upstream end of said seal, has a succession of ripples.

14. The connector according to claim 1, wherein the elastic seal avoids contacting side walls of the chamber in an uncompressed position.

15. The connector according to claim 1, wherein all or part of a wall of the ring is in sliding contact with a corresponding wall of the chamber throughout the movement of the elastic seal from a rest position of said seal to a compressed position of said seal.

16. The connector according to claim 1, wherein the chamber has at least two compartments with different cross sections, said compartments comprising a central compartment having a constant inner cross section, at least in a zone corresponding to a stroke of the ring, and a terminal compartment comprising the terminal end, having a smaller and constant or variable second inner cross section relative to said cross section, the ring extending partly into the central compartment.

17. A connector for medical use comprising:
    an adapter equipped at its centre with a needle extending into a chamber and terminating in a terminal part of said chamber, said terminal part having a cross section suitable for receiving, by friction, a luer type male connector at least in a terminal part of the needle including at least one orifice thereof being encased in a cavity an elastic seal having, in the thickness of its free end, a slit or equivalent, the elastic seal having a free end at a tangent to a terminal end of the chamber, said terminal end being at a longitudinal endpoint of said chamber;

a ring encircling a terminal part of said seal at least as far as a zone opposite the at least one orifice of the needle, the ring located inside the chamber, wherein said ring comprises two longitudinal portions having different cross sections; and said two longitudinal portions of said ring comprising a first cylindrical portion encircling a terminal part of said seal along a length corresponding to a length of said terminal part of said chamber, and a second portion having a second cross section substantially equal to a corresponding cross section of a central part of said chamber, said central part located further away from said terminal end relative to said terminal part.

18. The connector of claim 17 wherein said seal comprises a conical shape having a plurality of successive ripples extending from an upstream end of said seal to a collar of said seal.

19. The connector of claim 17 wherein the inner cross section of the terminal part has a 6% luer taper.

20. The connector of claim 1 wherein said ring is separate from said seal.

* * * * *

UNITED STATES PATENT AND TRADEMARK OFFICE
CERTIFICATE OF CORRECTION

| | | |
|---|---|---|
| PATENT NO. | : 8,152,790 B2 | Page 1 of 1 |
| APPLICATION NO. | : 12/065400 | |
| DATED | : April 10, 2012 | |
| INVENTOR(S) | : Lopez et al. | |

It is certified that error appears in the above-identified patent and that said Letters Patent is hereby corrected as shown below:

Title Page;
In the Abstract (57), Fifth line: change "The needlea terminal part" to --The needle has a terminal part--

Signed and Sealed this
Twenty-sixth Day of June, 2012

David J. Kappos
*Director of the United States Patent and Trademark Office*